United States Patent [19]

Schave

[11] Patent Number: 5,726,749
[45] Date of Patent: Mar. 10, 1998

[54] METHOD AND APPARATUS FOR INSPECTION AND EVALUATION OF ANGULAR DEVIATION AND DISTORTION DEFECTS FOR TRANSPARENT SHEETS

[75] Inventor: Richard D. Schave, Perrysburg, Ohio

[73] Assignee: Libbey-Owens-Ford Co., Toledo, Ohio

[21] Appl. No.: 717,112

[22] Filed: Sep. 20, 1996

[51] Int. Cl.⁶ .......................... G01N 21/00; G01N 21/84
[52] U.S. Cl. ............................................ 356/239; 356/430
[58] Field of Search ........................ 356/239, 237, 356/238, 430, 431, 371; 250/559.45, 559.46, 559.48

[56] References Cited

U.S. PATENT DOCUMENTS

| | | |
|---|---|---|
| 2,735,331 | 2/1956 | McMaster et al. |
| 3,166,627 | 1/1965 | Obenreder. |
| 3,792,930 | 2/1974 | Obenrder ............................ 356/239 |
| 3,855,332 | 12/1974 | Bridges ......................... 250/559.45 |
| 4,249,823 | 2/1981 | Task ................................. 356/239 |
| 4,299,482 | 11/1981 | Task ................................. 356/124 |
| 4,377,341 | 3/1983 | Task et al. ....................... 356/239 |
| 4,398,822 | 8/1983 | Task ................................. 356/239 |
| 4,647,197 | 3/1987 | Kitaya et al. .................... 356/239 |
| 4,709,157 | 11/1987 | Shimizu et al. .............. 250/559.46 |
| 4,837,499 | 6/1989 | Malthy, Jr. ....................... 356/239 |
| 5,016,099 | 5/1991 | Bongardt et al. ................ 358/106 |
| 5,128,550 | 7/1992 | Erbeck ............................. 356/374 |
| 5,146,282 | 9/1992 | Guering et al. .................. 356/239 |
| 5,210,592 | 5/1993 | Bretschneider ................. 356/239 |
| 5,343,288 | 8/1994 | Cohen et al. .................... 356/239 |

Primary Examiner—Frank G. Font
Assistant Examiner—Amanda Merlino
Attorney, Agent, or Firm—Marshall & Melhorn

[57] ABSTRACT

An apparatus and method for inspecting pieces of glass and other transparent sheets for optical defects is provided. The inspection apparatus can be integrated directly into the production line. The inspection apparatus includes an electro-optic inspection of the total viewing area for each transparent sheet as the sheets are conveyed at the end of the production operation. The apparatus includes a plurality of laser light sources positioned on one side of the sheet of glass or other transparent material, and a corresponding plurality of lenses and photosensitive position detectors on the opposite side. Light beams are directed from the light sources through the transparent sheets to the lenses and the detectors. The angular deviation of each light beam which occurs as the light beam passes through the sheet generates a signal at each of the detectors. The signals generated by the angular deviation of the light beam from the optical axis are processed by a computer system to provide information regarding the angular deviation values for the transparent sheet. The distortion, determined by the rate of change of the angular deviation, is calculated and compared to preset distortion values to determine if the transparent sheet is acceptable from a quality standpoint.

30 Claims, 6 Drawing Sheets

METHOD AND APPARATUS FOR INSPECTION AND EVALUATION OF ANGULAR DEVIATION AND DISTORTION DEFECTS FOR TRANSPARENT SHEETS

BACKGROUND OF THE INVENTION

1. Field of the Invention

The present invention relates to a method and apparatus for evaluation of optical characteristics of transparent material, and more particularly, to an inspection apparatus integrated into a production line for measuring angular deviation of light beams passing through automotive glass and for calculating the rate of change of the angular deviation to determine the distortion. The apparatus is designed for use in a production line to test the optical quality of the glass and ensure compliance with quality control standards.

2. Summary of Related Art

During the manufacture of glass and other transparent materials, optical defects and deviations may be produced which render the glass optically imperfect. Optical imperfections are of special concern in automotive glass and other applications where optical defects are unacceptable from a quality control standpoint.

In automotive glass, distortion and other defects are a significant concern in the manufacture of the glass sheets and in the fabrication of laminated glazing window units. Laminated window units for automotive applications comprise two sheets of glass integrally bonded to an interlayer of plastic, generally a sheet of polyvinyl butyryl. In the fabrication of laminated glazing units, the two sheets of glass are formed by heating and pressing individual sheets into conformity with a mold, and then pairing the sheets for lamination. An alternative means of forming the two sheets is by gravity bending the sheets in pairs in order to insure that their configurations closely match.

In the automotive glazing field, glass sheets are bent to various curved forms for utilization by the vehicle manufacturers in windshields. The flat or curve tempered glass parts utilized for present day automobile side and rear window glazings also must conform to a predetermined configuration in order to properly fit into the opening in a vehicle body. Despite the best efforts through years of experience in bending glass, it is found that the bent sheets warp or sag during the heating and subsequent cooling during fabrication, which results in distortion causing optical imperfections. Distortion is also a concern in architectural applications, such as multiple sheet insulating glass.

Distortion is one of the optical quality parameters that has been identified for characterizing transparencies, such as automotive glass. Distortion in a sheet of glass may occur due to wedge variations caused by non-parallel glass surfaces, curvature variations caused by curvature variations during the bending and tempering process, and optical index defects caused imperfections in the glass composition.

Wedge variations, which are also referred to as non-parallelism, result in the angular deviation of light beams passing through the glass caused by the non-parallel surfaces of the glass. Wedge variations may occur in a single piece of glass when the opposite sides of a single sheet of glass are not parallel. Wedge variations also frequently occurs in laminated glass, where one or more of the surfaces of the two sheets of glass are not parallel to the other surfaces.

Distortion is also caused by curvature variations in the surface of the glass sheet as a result of the tempering process. The radius of the surface changes, which causes angular deviation of the light beam and distortion. For curvature variations, convex portions shrink, by reflection, an image and concave portions magnify an image. If the rate of change in the surface shape of the glass is large, the resulting increase or decrease in the lens power of the sheet of glass will cause an unacceptable level of distortion. Wedge variations and curvature variations are separate distortion factors which may coexist.

Optical index defects generally refer to variations in the composition of the glass or to defects in the glass, such as bubbles or stones. Changes in the lateral displacement generally occur when a light beam is directed through the defect or composition change in the glass.

Wedge variations occur in the glass formation, bending, and laminating processes. Curvature variations also occur during the tempering process. Optical index defects occur in batch preparation, melting or refining and results in the lateral displacement of a light beams passing through the glass. It is desirable to determine if an unacceptable amount of distortion is present in the glass, and to identify and to isolate problems in production which cause the distortion.

Distortion is mathematically defined as the rate of change of the angular deviation of a light beam across a glass or other transparency. Angular deviation of a light beam caused by wedge variations or curvature variations is measured by the angular deflection or change of direction of the light beam as it passes through the glass. Distortion in any piece of glass or other transparency may be determined by mapping, at a plurality of locations on the glass, the angular deviation of light beams as they are transmitted from the light source through the glass to the observer.

Angular deviation is different than the normal lateral displacement (lateral shifting) of the light beam as it passes through the glass. Whenever a beam of light passes through a piece of glass at an angle other than perpendicular to the face of the glass, lateral displacement of the beam by a relatively small and constant amount results. However, when a beam of light passes through the transparency at the same angle, but where the faces of the glass are non-parallel, both lateral displacement and angular deviation result. While lateral displacement is insignificant in automotive windshields, the angular deviation and distortion causes the distance between the real location of the object and its apparent (angular deviation) position to increase as the range of the object from the observer increases. Consequently, a method of quantifying the angular deviation and the distortion in a piece of glass to ascertain the severity of the distortion is important in automotive glass and other applications.

Distortion is typically analyzed based on the non-linear mapping of objects viewed through the transparency, such that the actual physical position of an object does not linearly correspond to its apparent location as seen through the glass or other transparency. In the case of a perfect non-distorting transparency, a square grid object would be reproduced as an identical square grid in the image plane. Where there are wedge variations, curvature variations, or optical index defects in the transparency, the square grid will be reproduced in a distorted form in the image plane.

One of the problems from a production standpoint is that optical imperfections are not always readily apparent to casual observation. Optical imperfections may be located in random areas of the glass sheet not ordinarily disposed in a direct viewing area.

In automotive applications, the aerodynamic styling of the glass, with substantial curvature and mounting angles, makes it very challenging to produce acceptable windshields from a quality control standpoint. The detection of optical imperfections is also very challenging. The windshield is installed in the vehicle in an inclined position so that the driver views the road at a significant angle to the surfaces of the windshield. The geometry of the window units, which include not only front windshields, but also side and rear windows and roof panels, is of critical importance in establishing optical quality necessary to meet automotive industry standards.

The existing methods and systems for detecting and measuring distortion caused by wedge variations or curvature variations are difficult to use, time consuming, and unreliable. The systems which are acceptable for use in a production operation are not very accurate or comprehensive. Optical imperfections remain difficult to detect and quantify during regular production operations.

Many of the test systems involve manual inspection procedures. A conventional inspection procedure involves a visual inspection from a distant position of a stripe pattern or grid pattern through the windshield or other piece of glass. The optical distortion in the glass can be visually determined by an inspector in viewing the pattern. The zone with the largest defect is located and a measurement of the distortion is made where the distortion is the greatest. However, quantitative standardization cannot be obtained and differences among inspectors prevents uniform inspection quality.

U.S. Pat. No. 2,735,331 to McMaster et al. discloses an inspection apparatus which used a point source of light, a concave mirror, and an opaque screen, and a photoelectric device for detecting glass distortion. Such a system was not suited for inspection of large pieces of automotive glass in regular production operations.

One of the early laser systems for determining optical distortion in glass is U.S. Pat. No. 3,792,930. Surface contours of a piece of glass were scanned and analyzed to determine if the optical distortion of the piece of flat glass was caused by surface distortion or by optical index distortion.

More recent inspection apparatus generally use projection techniques, either with a localized beam or by projecting a test pattern through a zone of the windshield. A technique using a localized beam, such as that of U.S. Pat. Nos. 4,249,823; 4,377,341; and 4,398,822; provides a precise measurement of the angular deviation of the light beams in passing through a specific location in the windshield. But such techniques require very long measuring periods to inspect the overall windshield, which is one of the concerns for inspecting windshields in a production line.

One test pattern apparatus for global inspection is described in U.S. Pat. No. 4,299,482. A Fourier transformation of the image of a striated screen requires the making of a photographic printing plate, which also makes such a technique unacceptable for continuous inspection during production.

U.S. Pat. No. 4,647,197 teaches the use of a pattern which is observed through a windshield by a special camera. The camera is scanned across the windshield a given speed, which makes it possible to measure the lines of the pattern in the direction of the scanning. The scanning data is used to calculate any areas with optical defects caused by distortion. This apparatus does not provide a global inspection. In addition, the observation in a single direction may cause an inaccurate estimation of the distortion. U.S. Pat. No. 3,166,627 discloses a method measuring the magnitude of an optical defect by measuring the intensity of the shadow illumination using rotating discs and a light sensitive element.

Additional projection techniques using a scan or matrix camera includes U.S. Pat. Nos. 5,016,099; 5,128,550; 5,146,282; and 5,343,288. In many cases, the shadowgraphic technique can obtain only one data point at a time and does not provide a complete analysis of the piece of glass for production operations. A limited number of readings were available for inspecting a piece of glass. In other cases, special positioning systems or lens systems are required to obtain information regarding optical quality.

An inspection system for matching of paired sheets of glass is described in U.S. Pat. No. 4,837,449. The displacement of a collimated light beam is monitored and the position of the glass sheets are manipulated until the distortion is eliminated. The apparatus detects areas in which the curvature of the two sheets do not match. The amount of stress which would be created in the glass by laminating the sheets together can be calculated.

U.S. Pat. No. 5,210,592 discloses a method for determining the optical quality of a piece of plate glass which requires two parallel incident light beams having a reciprocal spacing. The reflected light from the two surfaces of a single piece of glass are detected and evaluated for determining optical quality.

SUMMARY OF THE INVENTION

In accordance with the present invention, there is provided an apparatus and method for inspecting pieces of glass for optical defects. An object of the present invention is to provide an accurate and efficient inspection system which can be integrated directly into the production line used for the production of automotive glass and other transparent sheets. Distortion caused by wedge variations and curvature variations is detected and quantified for quality control procedures.

An object of the present invention is to replace the human judgment involved in inspecting and grading glass using the grid system. In addition, the inspection apparatus must be suited for use in a production line as opposed to a laboratory setting. The apparatus should be able to obtain the desired optical data of a transparent sheet in a single operation and within the measurement time determined by the production rate of the transparent sheets.

The inspection apparatus and method in the present invention provides for an accurate electro-optic inspection of the total viewing area for each transparent sheet as the sheets are conveyed from the end of the production operation. The transparent sheet may be a single sheet of glass or a laminated piece of glass. The apparatus and method are ideally suited for inspecting curved pieces of glass such as used in the automotive industry.

The apparatus includes a plurality of laser light sources positioned on one side of the sheet of glass or other transparent material, and a corresponding plurality of lenses and photosensitive position detectors on the opposite side. Light beams are directed from the light sources through the transparent sheets to the lenses and the detectors. Any wedge variations or curvature variations in the glass will causes an angular deviation of the light beam as it passes through the transparent sheet. The angular deviation of each light beam is detected by the detectors and a signal is generated based on the magnitude of the deviation. The signals generated by the angular deviation of the light beam from the optical axis are processed by a computer to calculate the distortion based on the rate of change of the angular deviation across the transparency. The angular deviation and distortion are analyzed to provide information regarding the optical quality of the transparent sheet.

The transparent sheets are conveyed on narrow, parallel belts such that the sheets are fully supported by the belts and the viewing area of the glass is exposed for inspection purposes. The conveyor transports the sheets in a generally vertical configuration. The light sources are positioned beneath the conveyor such that the beams of light are directed through the surface of the glass at the approximate viewing angle at the time of installation. The lenses and detectors are positioned above the conveyor.

The lights sources, lenses, and detectors are mounted on horizontal cross members of a pivotable frame. The frame is mounted on a base and the conveyor passes through the center aperture of the frame. The frame can be pivoted on the base so that the beams of light from the light sources pass through the transparent sheets at the desired angle while maintaining the proper alignment of the light sources with the lenses and the detectors.

The laser light sources are secured to a cross beam of the frame in a linear configuration. The lenses and detectors are mounted on a similar cross beam and aligned such that light beams from the light sources are focused at the center of the photosensitive position detectors when no transparent sheet is present. Once the components are properly aligned and positioned on the frame, such components remain in alignment when the frame is pivoted to achieve the desired viewing angle.

When the transparent sheet is positioned between the light sources and the lenses and detectors, the light beams are deflected from the initial position on the detector. The detector generates a signal base on the occurrence of a non-centered light beam caused by the angular deviation of the light beam in passing through the transparent sheet. The signals are converted from an analog to a digital signal and are transmitted to a computer for storage and processing.

From a quality standpoint, the goal is to detect wedge variations caused by thickness variations and non-parallel surfaces in the transparent sheet, and curvature variations caused by a change in the radius of the surface of the transparent sheet, which would cause an unacceptable level of angular deviation and distortion. The angular deviation in the transparent sheet at a point in the path of the light beam can be calculated directly as a function of the distance of the deviation of the light beam at the detector and the focal length of the lens.

Once the angular deviation of the transparent sheet is determined, the next consideration is to determine and evaluate the distortion caused by the rate of change of the angular deviation in the transparent sheet. In the present invention, the angular deviation signals from two points in close proximity on the transparent sheet are used to calculate a distortion value in millidiopters. Numerous distortion values are calculated for each light source and detector as the transparent sheet passes through the light beams.

The positioning of the light sources can be in linear configuration or in an array. With the linear configuration, the light sources are spaced so as to form a linear set of light beams transverse to the path of the conveyor through which the transparent sheet passes on the conveyor. The speed of the conveyor may be controlled and monitored by the computer. As the transparent sheet is passed through the beams of light, the detectors transmit signals to the computer to provide optical information regarding points throughout the total viewing area of the transparent sheet. Although a linear positioning of the light sources works well in a conveyor application, the light sources can be arranged in any manner. A two dimensional array of appropriately spaced light sources could also be used to provide signals for determining optical defects. The light sources may be off-set to provide more complete scanning coverage as the transparent sheet passes through the beams of light from the light source.

As each transparent sheet passes through the beams of light, the output signals from the detectors are stored in buffer of the computer and processed to determine the optical qualities of the transparent sheets. The angular deviation values and the distortion values of each transparent sheet are calculated and mapped by the computer. Numerous output formats are available for reviewing and analyzing the optical data. The output data is displayed on monitors or printed out on printers.

The apparatus also includes a key board to input and store production information and test parameters in the computer. Ranges of acceptable values for the optical quality data can be utilized such that an alarm will be triggered when the values of the actual optical data exceed the range of acceptable values. For curved pieces of glass, such as automotive windshields, the range of acceptable values can be set at different values for various sections of the glass. The range of acceptable values and the comparison process for triggering an alarm can be conducted on a section by section basis.

An object of the present invention is to provide an apparatus that can be used in the production process for accurate inspection of each transparent sheet. The computer receives the signals from the detectors and processes such signals by calculating the angular deviation and distortion for each sheet within the allotted production time. By eliminating the handling or special positioning of the glass, and by the simultaneous processing of signals from multiple detectors, the global surface of the transparent sheet can be analyzed and a decision made as to acceptability of optical qualities of the transparent sheet.

Another object of the present invention is to develop an apparatus which can be adjusted in a production line installation for the inspection of transparent sheets with different curvatures. For automotive glass inspection, it is essential that the pieces of glass be inspected at the viewing angle as used in the automobile. In a highly competitive industry with end user demands for improved quality and just-in-time delivery, the inspection apparatus must be easy to set up and align during production model changes. The pivotable frame of the present invention allows the viewing angle to be adjusted without having to individually reposition the light sources or the lenses and detectors.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

DESCRIPTION OF THE PREFERRED EMBODIMENT

Figure 1:
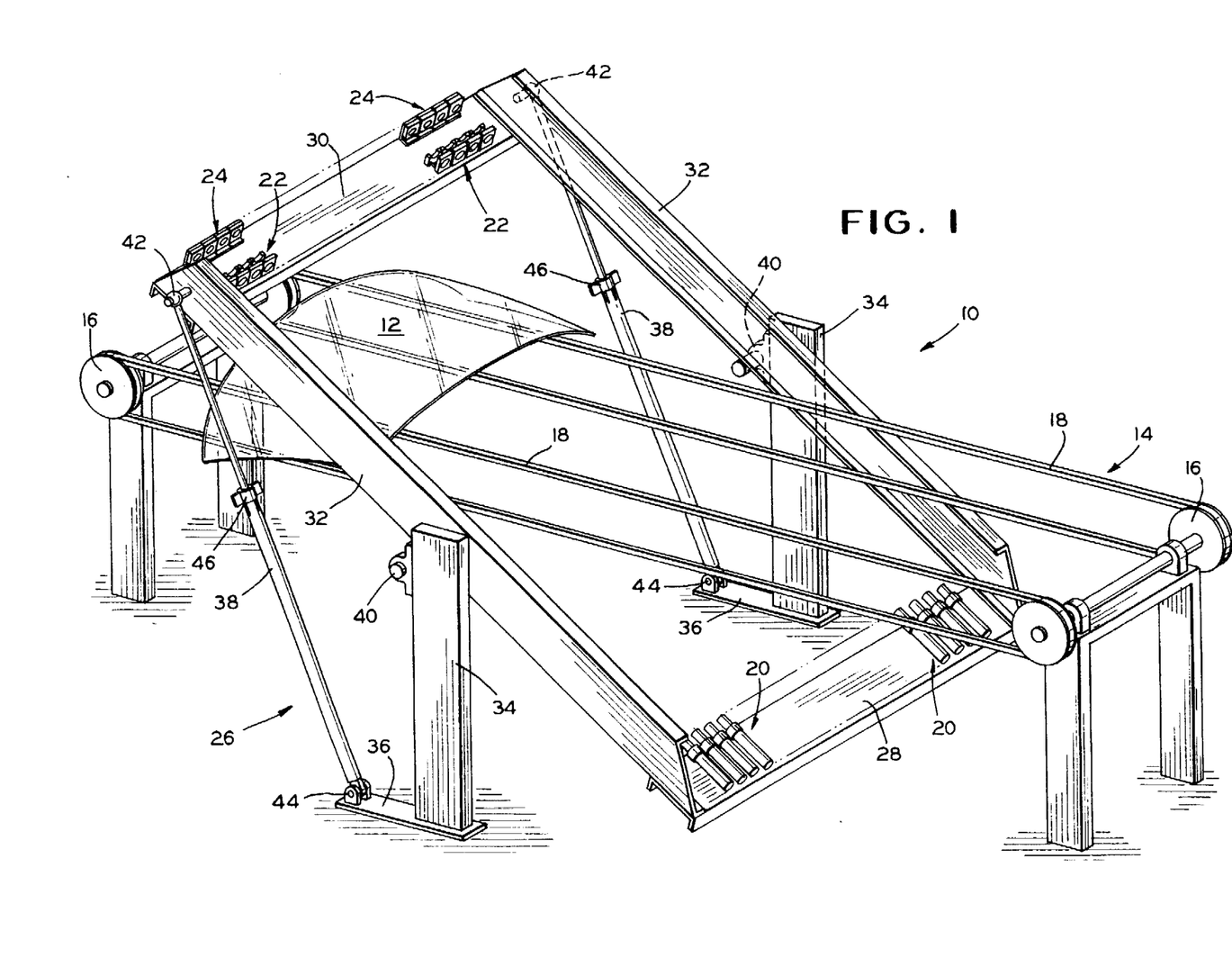
FIG. 1 is a schematic perspective of a system for practicing the invention.

Referring now to the drawings, FIG. 1 shows the inspection apparatus 10 of the present invention prior to inspection of a transparent sheet, such as an automotive windshield 12, positioned on the inspection conveyor 14. The inspection apparatus 10 transmits beams of light through the transparent sheet 12 as it passes through the apparatus 10 to provide for the measurement of angular deviation caused by wedge variations and/or curvature variations in the transparent sheet 12. The rate of change of the angular deviation is then used to calculate the magnitude of the distortion in the transparent sheet 12.

The inspection conveyor 14 is integrated into the production line such that transparent sheets of glass 12 are transferred onto the conveyor belts 18 at one end of the conveyor 14, conveyed through the inspection apparatus 10, and transferred from the conveyor at the opposite end. A variable speed conveyor drive (not shown) is used to drive the drive shafts and pulleys 16 on which the belts 18 are mounted. The spacing between the belts 18 can be adjusted by adjusting the spacing between the pulleys 16 on the drive shafts. The conveyor drive typically includes a variable speed motor, gear reduction mechanism, endless chain drive, and timing belt. Other variable speed conveyor drives may be used to drive the conveyor belts 18 to convey the transparent sheets 12.

The inspection apparatus 10 includes a plurality of light sources 20 which may be arranged in a linear configuration or an array. Each light source 20 directs a beam of light through the lens 22 such that the beam of light is focused at the center of the corresponding photosensitive position detector 24 before the transparent sheet 12 is positioned between the light sources 20 and the lenses 22. A pivotable rectangular frame 26 is integrated into the production line and forms an aperture through which the conveyor 14 transfers the transparent sheet 12. The light sources 20 are mounted on cross beam 28 of frame 26 which extends across the bottom of the conveyor belts 18. The lenses 22 and detectors 24 are mounted on cross beam 30 at the opposite end of the frame 26. The side members 32 of the frame 26 are mounted on vertical base member 34 with base plate 36.

The light sources 20 are positioned such that the light beams are directed through the transparent sheet of glass 12 at the same approximate angle that a driver or passenger in an automobile would be viewing the glass. Since the curvature and angle of viewing varies depending on the mounting in the automobile, it is generally necessary to adjust the angle at which the light beams from the light sources 20 pass through the transparent sheet 12. The side arms 32 of the frame 26 pivot about stub shafts 40 on the vertical frame 34. The adjustable support arms 38 provides stability to the frame 26. The adjustable support arms 38 pivot about top connector 42 and base connector 44 and include a locking mechanism 46.

When the locking mechanism 46 is loosened, the frame 26 can be pivoted about pivot point 40 until the desired viewing/installation angle is achieved for testing purposes. The viewing angle for testing on the inspection apparatus 10 is set at the same angle as the transparent sheet 12 would be viewed when installed in the vehicle. The light sources 20, lenses 22, and photosensitive position detectors 24 remain in alignment as the frame 26 is adjusted. Once the desired viewing angle is achieved, the locking mechanism 46 is tightened to secure the frame 26 at the desired angle relative to the transparent sheet 12 on the conveyor 14. When a production change takes place to produce a different model of transparent sheet 12 on the same production line, the only mechanical adjustment required for the inspection apparatus 10 is to pivot the frame 26 to the proper viewing angle. A positioning motor could be added to the frame 26 to provide for computer controlled positioning of the desired viewing angle.

Since the concave surface of the transparent glass sheet 12 is typically face down on the conveyor 14, the light sources 20 are positioned below the conveyor belts 18. If the pieces of glass 12 needed to be conveyed with the concave surface facing up, the light sources 20 may be positioned above the conveyor belts 18 and the lenses 22 and detectors 24 below the conveyor belts 20. Since a global inspection of the transparent sheet 12 on the conveyor 14 is available, the leading edge of the sheet 12 into the field of light beams may be any of the edges. The actual orientation of the sheet 12 on the conveyor 14 is inputted as part of the control parameters such that the output format and alarm triggers are properly determined. The viewing angle for each transparent sheet is also checked and adjusted at the start of a production run.

The transparent sheets 12 may also be mounted or conveyed in special fixtures (not shown) to provide more specific orientation. For example, in a front windshield, it is desirable to measure the distortion that a driver setting at the left hand side of the windshield would observe looking cross-court to the right hand side of the windshield. Since the side edges of the windshield are curved, distortion is an important concern at such a viewing angle.

Figure 2:
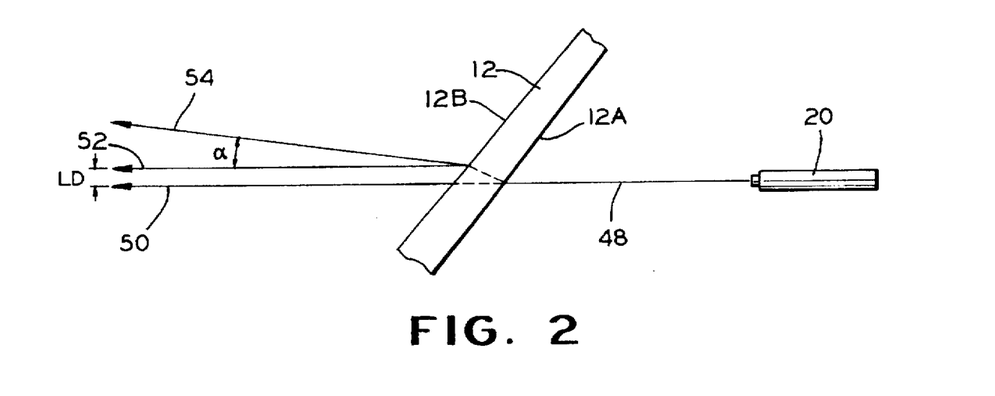
FIG. 2 is a schematical representation of the lateral displacement and angular deviation of a beam of light passing through a transparent sheet having non-parallel opposite faces and curvature.

In FIG. 2, the light source 20 is positioned at a viewing angle for a transparent sheet 12, such as an automotive windshield. A light beam 48 is directed from the light source 20 through the transparent sheet 12. The light beam 48 is a narrow, collimated beam centered about optical axis 50, which is the straight line path of the light beam 48 when no transparent sheet is present. Whenever a light beam 48 passes through the transparent sheet 12 at an angle other than perpendicular to the surface, the light beam 48 is laterally displaced from the optical axis by a relatively small and constant amount based on the optical index and viewing angle of the transparent sheet 12. When only lateral displacement is present, the displacement beam 52 travels parallel to the optical axis 50. If the opposite faces 12A, 12B of the transparent sheet 12 are non-parallel, if the two sheets of a laminated windshield are non-parallel, or if the surface of the sheet has a changing radius of curvature, angular deviation of the light beam will occur. The rate of change of the angular deviation is the measurement for the distortion.

As shown in FIG. 2, light beam 52 is caused by lateral displacement only and light beam 54 is caused by a combination of lateral displacement and angular deviation. In automotive windshields, lateral displacement in light beam 52 based on the optical index of the windshield remains constant with distance. When distortion is present in automotive windshields and other transparent sheets, such distortion can deceive a person viewing objects through the automotive windshields. The distortion increases with distance such that the difference between the real location of an object along optical axis 50 and its apparent position along light beam 54 increases as the range of the object from the viewing source 20 (such as a person in an automobile) increases.

When inspecting automotive glass and other transparent sheets, the apparatus 10 of the present invention is designed to determine defective glass based on the presence of the presence of angular deviation ($\alpha$, the angle between beam 52 and beam 54). Angular deviation is caused by non-parallel surfaces 12A, 12B in a single sheet or non-parallel surfaces in two pieces of glass laminated together, or by curvature variations. Once the angular deviation is known, the change in the angular deviation can be used to calculate the distortion as a function of lens power.

Figure 3:
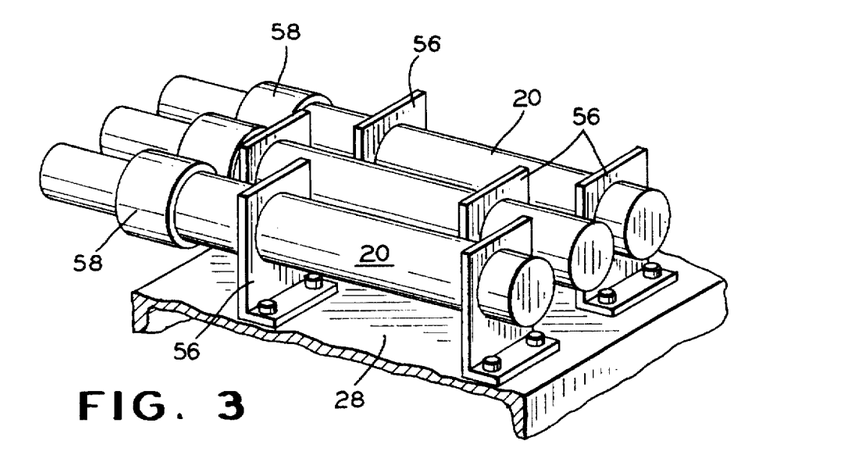
FIG. 3 is a perspective view of the laser light sources mounted in parallel, spaced apart relationship.

In the inspection apparatus 10, a highly collimated light source 20, the lens 22 and a position sensing photosensitive position detector 24 can be used to measure the angular deviation when a light beam passes through the transparent sheet 12. The preferred light source shown in FIG. 3 is a helium-neon laser light source 20. The laser light source 20 is polarized and provides a concentrated beam of intense collimated light which is preferred from a detection standpoint. The light source is securely mounted to the cross beam 28 by brackets 56. The light sources 20 must be maintained in a stable position to ensure accurate positioning of the light beams over an extended period of production operations. A beam expander 58 is mounted on the output end of the light source 20 to provide a more stable beam. The light beam is expanded such that the beam diameter is approximately one-eighth inch when passing through the glass sheet 12. The light beams are maintained in parallel, spaced-apart relationship to minimize any interference from adjacent light sources 20. For an automotive windshield assembly line, system 10 includes approximately thirty-two light sources 20 linearly arranged with two inch spacing. Diode laser or conventional collimated light sources could also be used to provide the required source of light.

The light sources as shown in FIG. 1 and FIG. 3 are arranged to form a linear pattern of light beams through which the transparent sheet 12 will pass. Additional rows of light sources 20 or other arrangement of multiple light sources 20 could be positioned to provide an array or matrix of light sources directed at a transparent sheet 12. When the spacing in a single row is set at two inches, the optical index defects are more difficult to detect. By off-setting additional rows of light sources in a matrix configuration, the inspection apparatus 10 could be used to detect optical index defects as well as wedge variations and curvature variations. Even with a single row of light sources 20, optical defects will generally cause significant distortion which is detected by the inspection apparatus.

Figure 4:
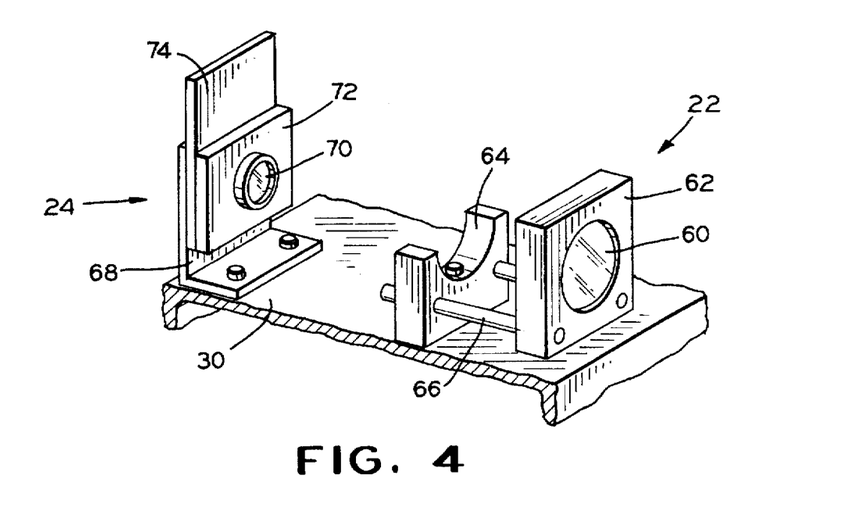
FIG. 4 is a perspective view of the corresponding lenses and photosensitive position detectors for measuring the deviation of the light beams.

The mounting of the lenses 22 and photosensitive position detectors 24 on cross beam 30 is shown in FIG. 4. The lenses 22 are provided with an adjustable position device and include a glass focusing lens 60 secured by a frame 62 in a base 64. Adjustable mounting pins 66 are used to position the lens 60 at a specific distance from the photosensitive position detector 24 mounted on bracket 68. Typical lenses are achromatic lenses with a focal length of 250 millimeters.

The distance between the lens 60 and the sensing surface 70 at the detector aperture is set at the focal length of the lens 60 such that the light beam from a light source 20 is focused at the sensing surface 70. The photosensitive position detector 24 includes a plate 72 with a center aperture and control circuit board 74 for generating signals based on the position of the focused light beam entering the aperture of the plate 72 to reach the sensing surface 70.

Figure 5:
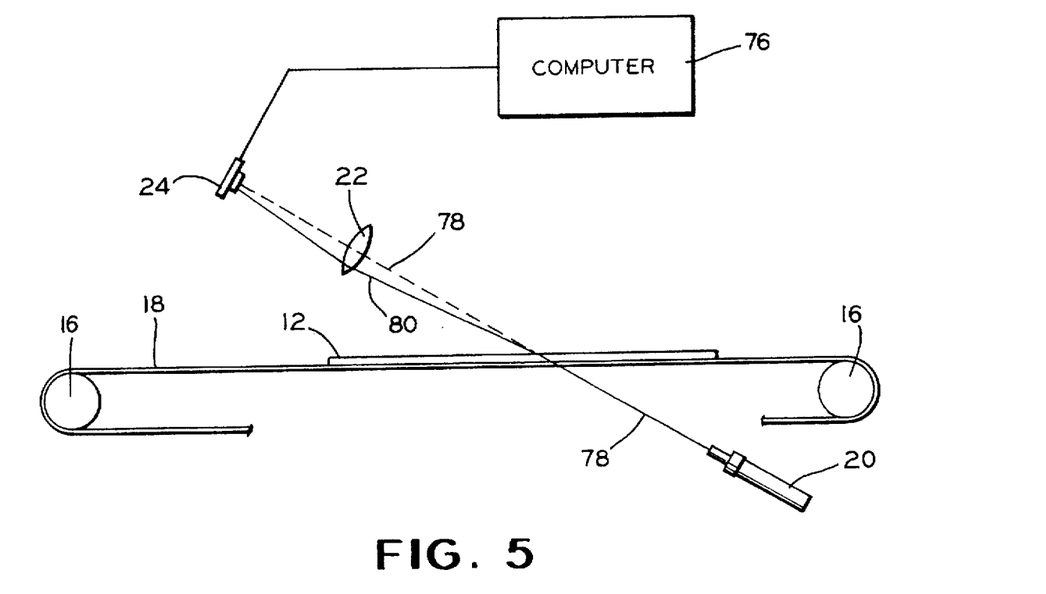
FIG. 5 is an enlarged schematic view illustrating the paths followed by the beams of light in passing through a transparent sheet of glass.

As shown in FIG. 5, a light beam 80 from the light source 20 is initially directed to the center of sensing surface 70 of the detector 24 along optical axis 78. When the light beam 80 is deflected from the optical axis 78, the sensing surface 70 of detector 24 generates a horizontal displacement signal and a vertical displacement signal to accurately determine the position of the light beams striking the detector 24. The signals from the photosensitive position detectors 24 are transmitted to an analog to digital converter at the computer 76 for processing and storage. In a system for testing automotive windshields, the size of the sensing surface 70 is approximately four square millimeters.

The basic operation for detecting distortion caused by the angular deviation of the light beams is shown in FIGS. 5 and 6A–6F. Although only a single light source 20 is shown in FIG. 5, the operation would be the same for all of the light sources 20 mounted in the inspection apparatus 10. The light beam 80 is initially aligned in the center 82 of the detector 24 along the optical axis 78. The light beam 80 does not have to be centered on the detector since the computer 76 can determine the zero point or starting point of the light beam 80 prior to operation and detect changes in the position of the light beam 80 from such zero point. The zero point may be intentionally set at a point other than the center 82 of the detection surface 72 so that the range in order to provide a broader protection range in a specific direction.

The transparent sheet 12 is conveyed by conveyor belts 16 through the light beam 80. The lens 22 may be positioned at any distance from the point in the transparent sheet 12 through which the light beam 80 passes. In automotive applications, distance is approximately one meter, which minimizes the interference to the light beams and provides the desired detection signal sensitivity. The light beam 80 is generally positioned at a slight angle to the transparent sheet 12. This results in lateral displacement of the light beam 80 from the optical axis 78 as the light beam 80 passes through the transparent sheet 12.

When the light beam 80 transmitted from the surface of the transparent sheet 12 departs from the optical axis 78, such departure is generally the result of lateral displacement caused by the angled positioning of the transparent sheet 12, or angular deviation caused a wedge variation (non-parallel surfaces) and/or a curvature variation (changing radius in the surface of the sheet 12). When the photosensitive position detector 24 is positioned in the focal plane of the lens 22, the detector 24 is insensitive to lateral displacement and the departure of the light beam 80 from the optical axis 78 at the detection surface 70 of the detector 24 is caused only by angular deviation.

The sensitivity of the apparatus 10 is effected by the size of the detector 24 and focal length of the lens 22. To measure large angular deviations, the detector 24 is spaced in close proximity to the transparent sheet 12. To measure small angular deviations, the detector 24 is positioned at a greater distance from the sheet 12. For automotive windshields, the preferred distance between the transparent sheet 12 and the detectors 24 is between one to two meters. This provides sufficient space to pass a windshield through the system 10. Such proximity also minimizes the undesirable vibration and movement of the system 10 during production operations, and the impact of light and air interference. Such spacing is conducive for integration of the apparatus into a production line and provides sufficient sensitivity to detect any unacceptable angular deviation caused by wedge variations or curvature variations.

Figure 6A:
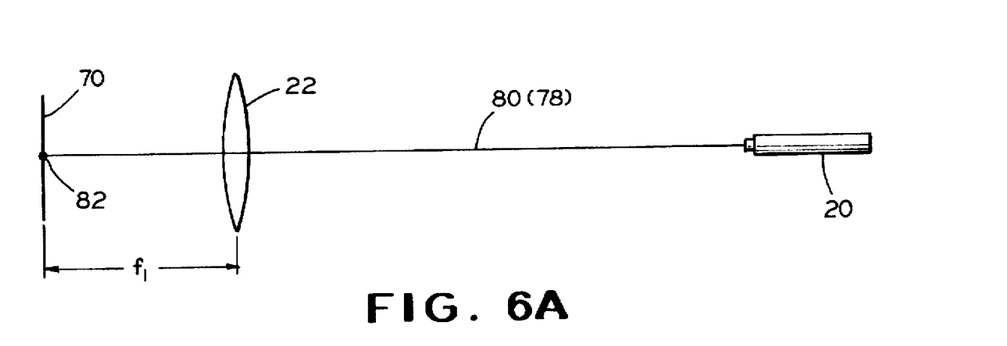
FIGS. 6A–6F are enlarged schematic views showing the path of the light beam from the light source to the photosensitive position detector, 6A showing the optical axis, 6B showing no distortion, 6C showing standard lateral displacement only, 6D showing angular deviation caused by a wedge variation, 6E showing angular deviation and standard lateral displacement, and 6F showing angular deviation cause by a curvature variation.
Figure 6B:
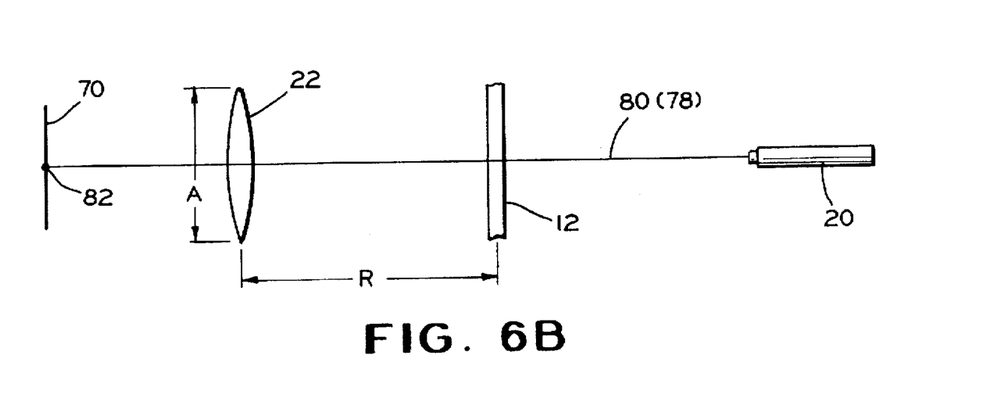

FIGS. 6A–6F show schematic diagrams of the basic optical configuration and angular deviation measurement capabilities. In FIG. 6A, the light beam 80 defines the optical axis 78 which is aligned with the center 82 of the detection surface 70 without any transparent sheet in the path of the light beam 80. The center 82 of the detection surface 70 is positioned at the focal point of the lens 22. In FIG. 6B, when a transparent sheet 12 with parallel surfaces is inserted perpendicular to the path of the light beam 80, no deviation from the optical axis 78 occurs.

Figure 6C:
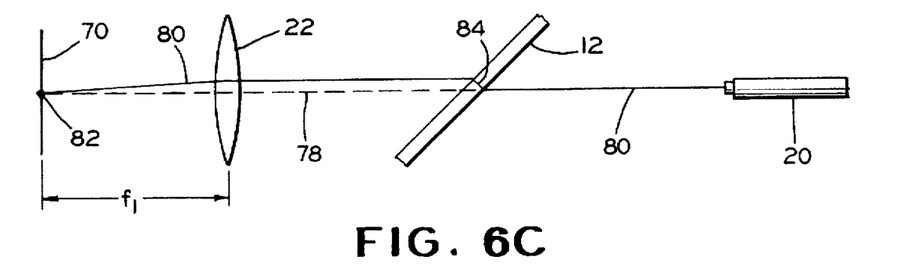

In FIG. 6C, insertion of the transparent sheet 12 at an angle causes a lateral displacement 84 of the light beam 80. The lens 22 and the detector 24 are positioned at a distance equal to the focal length of the lens 22, which causes the lateral displacement to be suppressed. By definition, all lateral displacement contributions are parallel to the optical axis 78. The effect of the lateral displacement 84 is nulled at the focal point of the focusing lens 22. Light beam 80 is laterally displaced 84 as it travels through the transparent sheet 12 in FIG. 6C. Light beam 80 travels parallel to the optical axis 78 to focusing lens 22 and then strikes the detector sensing surface 70 at the center 82. Even if a defect in the transparent sheet 12 further deflects the path of the light beam 80, the lateral displacement contribution is parallel to the optical axis 78 Thus, by spacing the lens 22 and the detector 24 at the focal length of the lens 22 to remove the effects of lateral displacement, any deviation of the light beam from the center 82 of the detection surface 70 is caused by angular deviation of the light beam 80.

Figure 6D:
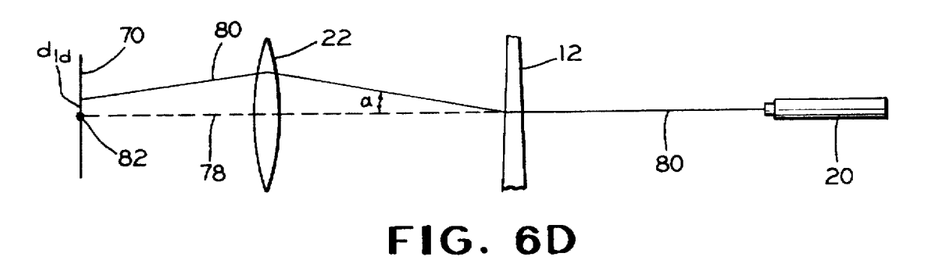

FIG. 6D shows the angular deviation of the light beam 80 caused by a wedge variation, the non-parallelism of surfaces 12A and 12B of the transparent sheet. The light beam 80 deviates from the optical axis 78 at an angle $\alpha$. Since the light beam 80 is not parallel to the optical axis 78, the light beam 80 is not focused at the focal point at the center 82 of the detection surface 70. The deviation $d_{1d}$ from the focal point at the center 82 of the detection surface 70 is sensed by the detector 24 and signals are generated based on the position of the light beam 80.

Figure 6E:
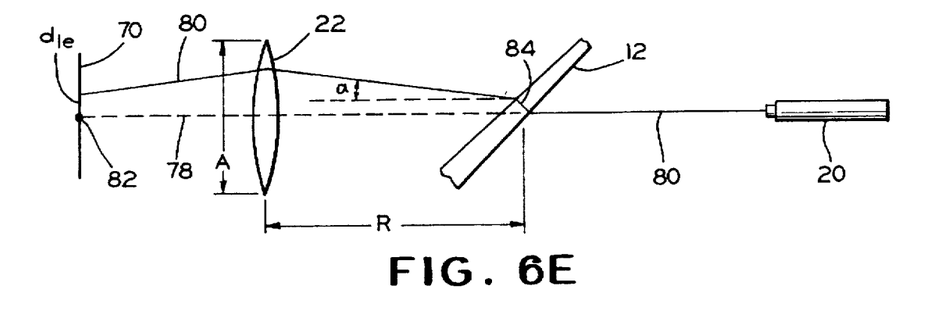

In FIG. 6E, a transparent sheet 12 with a wedge variation is positioned at an angle. The light beam 80 includes both lateral displacement and angular deviation which results in a deviation from the focal point at the center 82 of the detection surface 70. The lateral displacement 84 in FIG. 6E is the standard displacement caused by the angular positioning of the transparent sheet 12. Such lateral displacement 84 component is suppressed as noted above. The resulting deviation $d_{1e}$ is dependent only upon the angular deviation $\alpha$ caused by the wedge variation.

Figure 6F:
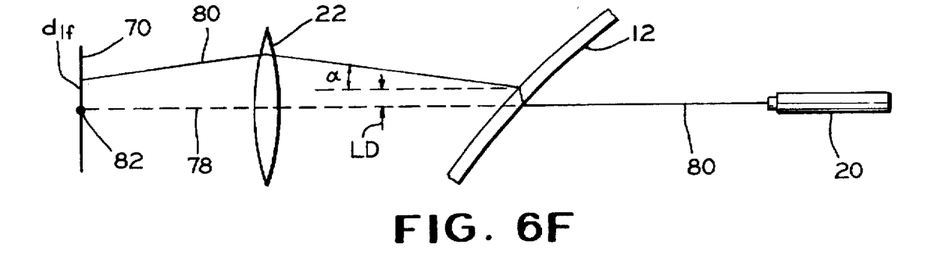

In FIG. 6F, the transparent sheet 12 includes a curvature variation and is positioned at an angle. The light beam 80 includes both lateral displacement 86 and angular deviation caused by the curvature variation. The lateral displacement is suppressed and the angular deviation results in the light beam being displaced from the focal point at the center 82 of the detection surface. The resulting deviation $d_{1f}$ is dependent upon the angular deviation caused by the curvature variation.

Angular deviations caused by wedge variations and angular deviations caused by curvature variations are separate distortion factors which may coexist in a transparent sheet such as a windshield. The wedge variations occur primarily in the laminated glass. The curvature variations occur in the bending and tempering of the glass. By detecting and quantifying the angular deviation, the distortion, which is the rate of change of the angular deviation, can be calculated.

The optical configuration of the inspection apparatus 10 requires consideration of conventional optical constraints. One major restriction relates to the aperture diameter of lens 22 in relation to the distance R between the transparent sheet 12 and the lens 22. The maximum combination of lateral displacement LD and angular deviation $\alpha$ imparted to the light beam 80 from its normal position along the optical axis 78 must not deflect the light beam 80 outside the periphery of the lens 22. Mathematically this constraint is described by the following relationship:

$$(LD+R \tan \alpha) \leq A/2$$

where LD is equal to the lateral displacement, R is equal to the distance between the transparent sheet 12 and the lens 22, $\alpha$ is the angular deviation, and A is the aperture diameter of the lens 22.

Angular deviation (refraction) is defined as the angular deflection or change of direction of a light ray as it passes through the transparency. Angular deviation does not include lateral displacement. For small angles, the angular deviation $\alpha$ is given by $$\alpha = d_1/f_1$$

where $d_1$ is the displacement distance from center on the photosensitive position detector 24 and $f_1$ is the focal length of the lens 22. Since the focal length $f_1$ is constant, the angular deviation $\alpha$ is directly proportional to the displacement distance $d_1$ from the focal point center 82 on the detection surface 70 of the photosensitive position detector 24.

By using a plurality of light sources 20 in the inspection apparatus 10 and passing the transparent sheet 12 through the beams of light 80, information regarding the viewing surface can be obtained in a single pass of the transparent sheet through the apparatus 10. The displacement distance $d_1$ is detected at each detector 24 and signals are transmitted to an analog to digital converter and the computer 76 for processing and storage. For automotive windshields, a two inch spacing of the light sources 20 provides sufficient information to evaluate the overall quality of the windshield. The computer stores a series of angular deviation readings for each detector during the transporting of the transparent sheet 12 through the light beams 80. Readings are taken at the rate of at least one per millimeter or more frequently.

Distortion, which is quantified based on the refractive lens power of the transparent sheet 12, is the rate of change of the angular deviation. The distortion of the transparent sheet 12 may be calculated for a plurality of surface segments by comparing the angular deviation of the light rays at a plurality of locations on the transparent sheet 12. In determining the lens power for various segments of the sheet, the spacing of the two points used to calculate the lens power is usually set in the range of 4 to 20 millimeters, with 6.35 millimeters being a preferred distance for testing automotive windshields.

Figure 7:
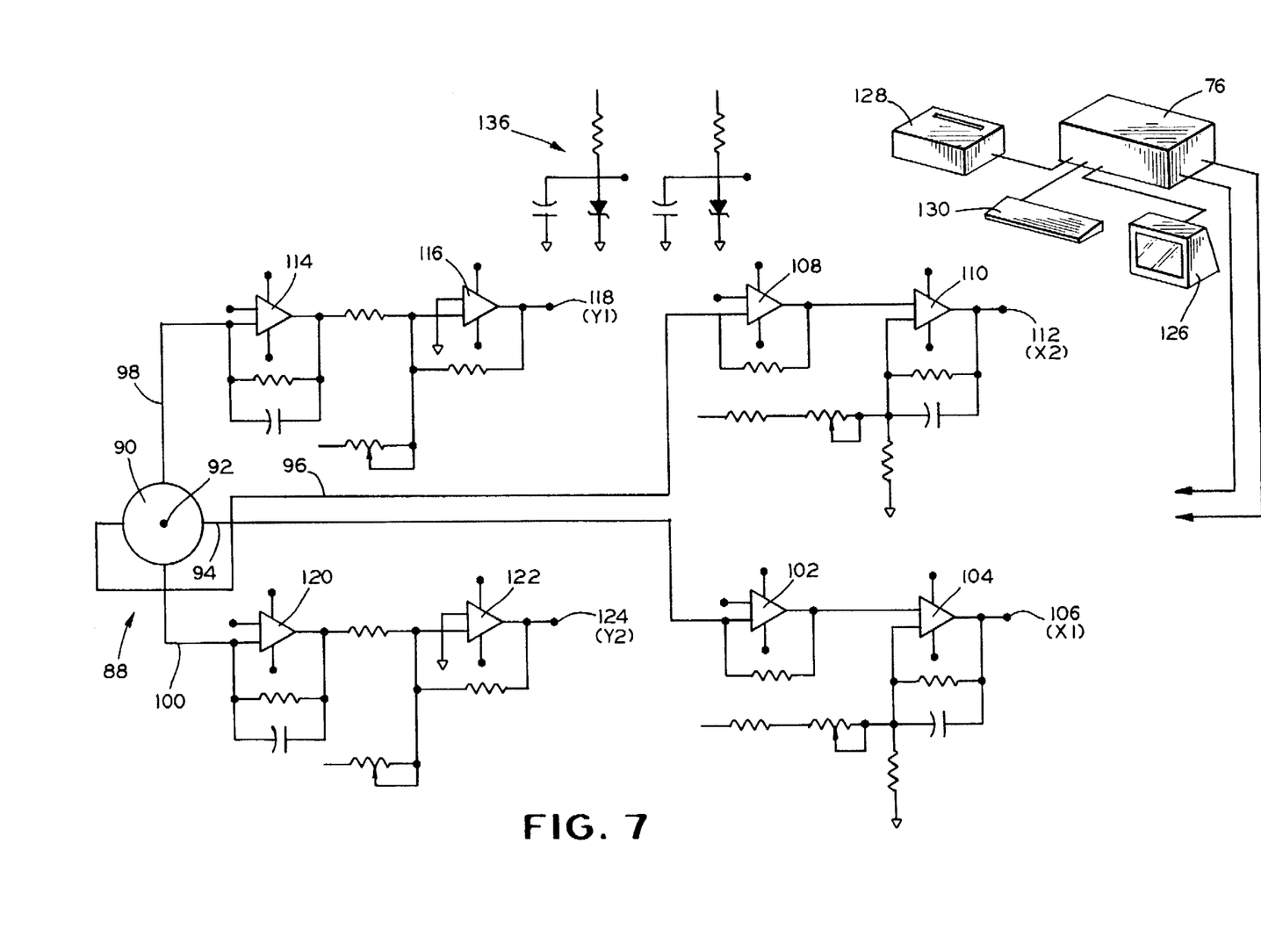
FIG. 7 is a schematic/block diagram of the control system for processing the signals from the photosensitive position detectors and processing of the data by the computer system.

One embodiment of an electronic network for the photosensitive position detectors 24 is shown in the block diagram of FIG. 7. Other photocell quadrant detectors or beam spacing measuring devices can be used to detect deviation from the optical axis 78 as the transparent sheet 12 travels on conveyor 14 through the light beams 80.

In FIG. 7, the photosensitive position detector includes a photodiode 88 with a detection surface 90 and a center wire 92. The photodiode 88 is of the PIN structure whose output is proportional to the position of the light beam impinging on the surface 90 of the photodiode 88. The center wire 92 is a bias to the photodiode. Four wires 94, 96, 98, 100 are equally spaced around the center connection 92. Two of the wires 94,96 are spaced on opposite side of the surface along the horizontal axis and the other two wires 98,100 are placed on the vertical axis. The photodiode material has a linear resistivity such that the light striking the photodiode 88 creates electron hole pairs which causes current to flow in each of the wires which is inversely proportional to the distance from the light beam. Consequently, the photodiode tracks the centroid of the light beam which strikes the surface 90.

The detectors 24 include circuitry mounted on circuit board 74 for generating a signal to be transmitted to an analog to digital processor (not shown) and computer 76 for processing. The output signal from positive horizontal wire 94 is transmitted to individual preamps 102, 104 and to output terminal 106 (X1). The signal from the negative horizontal wire 96 transmits a signal to preamps 108 110 with output terminal 112 (X2). The positive vertical wire 98 is connected to preamps 114, 116 to output terminal 118 (Y1). The final signal wire, the negative vertical wire 100, is transmitted to preamps 120,122 with output terminal 124 (Y2).

The photosensitive diode 88 is sensitive to changes in light intensity. In a production setting, light transmission may present problems. The sensitivity control 136 is used to calibrate the output signals and to adjust the output sensitivity of the preamps.

The output signals from all four output terminals 106, 112, 118, 124 may be transmitted to an analog to digital converter (not shown), which converts the signal for processing and storage by the computer 76. In order to simplify the processing required to calculate the distortion, the light from the laser light sources 22 is typically polarized in a vertical direction such that output from Y1 and Y2 are the only terminals which are used to generate signals for processing by the computer 76. The polarized light source minimizes internal reflections and interference patterns. A low pass filter may be used to suppress narrow streaks. Alternatively, a band pass filter may be used to suppress the extra wide lengths and provide a signal range which is conducive to comparison and correlation to the manual grid system used in the glass industry.

The computer determines angular deviation α based on the displacement distance at each detector 24 as represented by the output from the vertical output terminals Y1, Y2. The angular deviation value is calculated in micro-radians according to the formula $\alpha = d_1/f_1$ noted above, where $f_1$ is constant and $d_1$ is determined based on the following equation:

$$d_1 = [(V_{y2} - V_{y1})/(V_{y2} + V_{y1})] * h/2$$

where $V_{y2}$ and $V_{y1}$ are the voltage value of the signal from the output terminals Y1 and Y2, and h is the height of the detection surface 70.

The computer 76 is receiving the angular deviation displacement signals from each photosensitive position detector 24 as the transparent sheet 12 is passing through the light beam 80. The analog to digital converter triggers the readings such that up to 48 readings per inch can be obtained as the transparent sheet 12 passes through the light beam 80. The computer 76 is also receiving speed and position signals from the conveyor control system such that distance or timing between the points can be specified with a high degree of accuracy. As the transparent sheet is passed by the conveyor 14 through the beams of light 80, the digital signals from the analog to digital converter are stored in buffers of the computer 76 for further processing. The signals in buffer storage are processed by the computer 76 for analysis of the angular deviation values and the distortion values. Signals from all of the detectors 24 are processed simultaneously. The angular deviation values α are calculated and monitored for each detector 24 over the entire length of the transparent sheet 12 to provide angular deviation values for the total surface area.

Once angular deviations α have been determined for two points within a specified proximity as noted above, the distortion in millidiopters can be calculated based on the following formula for the calculation of lens power:

$$P = C * [\tan(\alpha_2 - \alpha_1)/s * \sin(I)]$$

where P is the lens power, which represents the magnitude of the distortion, C is a geometric constant, s is the distance between the two points used to obtain the angular deviation values $\alpha_2$ and $\alpha_1$, and (I) is the installation angle for the transparent sheet being tested. For automotive windshields, the preferred spacing s between the two points is approximately 6.35 millimeters. The number of distortion values to be calculated for each laser can be selected to provide a mapping of the distortion values throughout the surface of the transparent sheet 12. The preferred number of deviation values is approximately forty-eight readings per inch such that the computer 76 calculates and stores approximately 24 distortion values P and the number of lens power deviation values P calculated and stored by the computer 76 are approximately 24 per inch in the windshield applications of the present invention. Instead of calculating the distortion values P, a differentiating circuit could be added to the apparatus to directly determine the distortion as the rate of change of the angular deviation. From a cost and production standpoint for automotive windshields, the use of two angular deviation points to calculate distortion provides sufficient accuracy.

For windshields and other window glass products in production applications, the goal is to keep the lens power value for distortion as low as possible. The desired lens power value P for distortion quality is zero (0), indicating no positive magnification or negative magnification (shrinkage).

The distortion values P can be correlated to the automotive grid system grading currently used for inspection purposes in production operations. The magnitude of the distortion in millidiopters for various zones of the sheet 12 are within the acceptable range, then the sheet 12 is approved from a quality standpoint. In addition, control limits can be set in the computer 76 such that any angular deviation or any distortion value P outside of an acceptable range can be used to generate a signal in the production operation.

The computer 76 has a number of output formats to permit to display information on the monitor 126 or print out information on the printer 128. A keyboard 130 is provided to input trigger points, output format, and other information into the computer. For example, production information regarding the model number for the transparent sheet 12 and production identification information can be entered on the keyboard 130.

The output from computer 76 is also controlled at the keyboard 130. The angular deviation in the path of a single light source 20 can be selected at the keyboard 130 and plotted graphically on the printer 128. The output for each of the lens at a specific position can be requested to provide angular deviation or distortion information. Similar output information can be displayed on the monitor 126. The monitor 126 can also display a color-coded global map for the total surface of the transparent sheet 12. The deviation is calculated and displayed in micro-radians and the distortion is calculated and displayed in millidiopters.

Once the data is stored in the computer 76, the operator can specify the information from specific detectors 24 for monitoring and observation. For example, the angular deviation for a specific detector 24 could be plotted along the path of the light beam across the transparent sheet 12. The comparison of angular deviation for subsequent sheets 12 would allow the production operator to detect production changes before the angular deviation exceeded the acceptable range. An extensive amount of information regarding angular deviation and distortion is available and the access to such information can be controlled by the operator through the keyboard 130 and output devices 126, 128.

The inspection apparatus 10 can detect angular deviation and distortion for not only flat sheets, but also for curved sheets, such as automotive windshields. With the curved windshield designs used in automotive applications, the angular deviation and distortion will vary from area to area on the windshield. Consequently, a single trigger value for triggering an alarm when the angular deviation and/or distortion is outside of an acceptable range, is generally not adequate for inspection purposes. The computer 76 can process multiple alarm trigger points based on zone designations for various segments of the glass surface.

Figure 8:
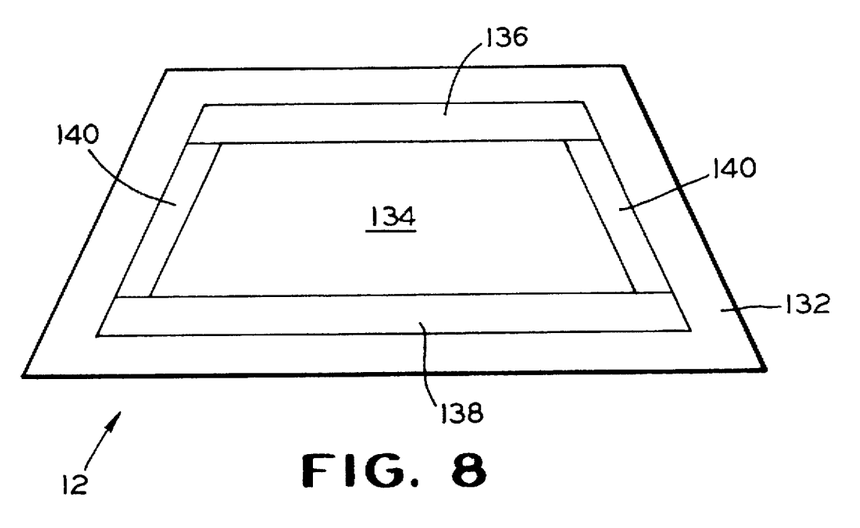
FIG. 8 is a schematic view showing the zones or section of a windshield for inspection analysis.

In FIG. 8, a transparent sheet 12, such as a windshield, is shown in schematic form. The windshield has been divided into inspection sections or zones. The outer edges 132 of the windshield 12 are not significant from a quality control inspection standpoint. The outer edges are covered when the windshield is installed, and are not used for viewing by the driver. The windshield 12 will generally include a primary viewing section 134 in the center of the windshield 12. The top section 136, bottom section 138, and the side sections 140 may have a high degree of curvature which causes some permissible distortion. The primary viewing area 134 is most important from an inspection standpoint and the range of acceptable values for angular deviation and distortion can be carefully controlled and monitored in the primary viewing area 162.

Alarm trigger value can be specified and stored in the computer 76 for each detector 24 in the linear configuration shown in FIG. 1. The alarm trigger values can be changed as the windshield 12 travels through the light beams. For example, a light source 20, lens 22, and detector 24 in the middle of the system may have three or four different alarm trigger values as the light beams from the bottom section 138 to the viewing area 134 and then to the top section 136. Similar components inspecting the side sections 140 or the outer edges 132 of the windshield may have only a single alarm trigger value.

By appropriately processing the data from the detectors, a numerical enumeration of the pertinent parameters of angular deviation and distortion is created in the form of a map of the transparent sheet. This map is compared by computer modeling with a corresponding map indicative of acceptability criteria parameters to determine whether the inspected transparent sheet falls within predetermined standards of acceptability. The inspection apparatus 10 can be used for both single sheets and for laminated glazing units.

The operation of the inspection apparatus 10 is designed for integration into a production operation. At the start of a production run for a specific model of transparent sheet 12, data for such model, such as alarm trigger values, can be programmed into the computer 76 and can be loaded into the processing system of the computer 76 by an operator at the keyboard 130. Before the arrival of the first transparent sheet 12, light beams 80 from each light source are centered at the center point 82 on the detectors 24. The sensitivity, light level, and range of the detectors are checked and adjusted.

A first transparent sheet 12 is deposited on one end of the conveyor 14 and is conveyed through the light beams 80 in a controlled manner by the computer 76 interface with the conveyor drive system. The signals from the detectors 24 are stored in buffer of the computer 76 and processed to determine if the actual values for angular deviation and/or distortion are outside of the alarm trigger range. The operator can select and monitor output data from the computer 76 during the production operation. In addition, the data may be stored for further processing and analysis at a later date.

After the transparent sheet 12 is passed through the light beams 80, the transparent sheet is retained at the opposite end of the conveyor 14 until the processing of information is complete and the next transparent sheet is deposited on the front end of conveyor 14. If the first transparent sheet 12 being discharged from the conveyor is within the acceptable range, the sheet 12 is ready for further processing and use. If an alarm is triggered, the sheet 12 may be diverted from the regular production line for detailed inspection and analysis.

When an alarm is signaled, the computer 76 provides output information to the monitor 126 or the printer 128. The specific light source 20 (or light sources) which triggered the alarm can be displayed. The angular deviation for such light sources 20 can be plotted to show where at what point in the inspection pass that the unacceptable deviation had occurred. In windshield production, distortion is frequently caused by bending the glass with too large a variation in radians. The data from the inspection system 10 can be used to adjust the production operation for bending the glass.

During the production of a laminated windshield, two sheets of glass are formed in the desired shape and then are paired for lamination. The distortion caused by the lamination material and the thickness of the material are known values. The distortion values can be determined for the unlaminated glass and the laminated windshield, including the inboard distortion and the outboard distortion. Once these values are determined for the individual pieces of glass and the laminated windshield, the lamination induced distortion, the curvature distortion, and the total laminated windshield distortion can be predicted. The two pieces of glass can be selected so as to minimize the total laminated windshield distortion.

The conveyance of the individual sheets 12 and the processing of the data can be accomplished in a matter of seconds. The conveyor 14 can transport the sheet 12 at a speed of over 30 inches per second. The system 10 can store approximately 234,000 inputs per second such that the processing time for the computer 76 can be completed within the allotted time for receiving the next sheet of in an automotive glass operation. The linear array of light sources 20, lenses 22 and detectors 24 provides global coverage of the sheet 12. During the processing of a typical windshield, approximately 1800 data points per laser are stored in the computer buffer. The inspection apparatus 10 and conveyor can easily be integrated into a production line such that each transparent sheet in the production process can be inspected. After the production run is completed, the data initially stored in the buffer may be stored in the computer 76 or on disk for further analysis or for maintaining a permanent record of the inspection data.

The accuracy and sensitivity of the inspection apparatus can be adjusted to achieve the desired inspection tolerances without a significant number of false alarm signals. Optical parameters, such as the spacing distance between the transparent sheet 12 and the lens 22, the focal length of lens 22 or the lens aperture size can be changed to achieve the desired inspection capabilities. The light intensity of the light sources and the detector circuits can also be adjusted. From a process standpoint, the number and positioning of the light sources 20 and corresponding lenses 22 and detectors 24 can be modified on the frame 26 such that global surface readings can be obtained within the allotted production time.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. Apparatus for evaluating the optical quality of a transparent sheet comprising:

positioning means for positioning a transparent sheet;

a plurality of light sources mounted adjacent said positioning means in spaced apart relationship for directing a plurality of light beams toward the transparent sheet;

a corresponding plurality of lenses for focusing the light beams, said plurality of lenses mounted opposite the transparent sheet from said plurality of light sources;

a corresponding plurality of photosensitive position detectors positioned at a focal point of said plurality of lenses and aligned with said plurality of light sources for detecting the light beams and for generating signals indicative of the position of the light beams;

a computer system in electrical communication with said plurality of photosensitive position detectors for processing the signals received from said photosensitive position detectors as said positioning means positions the transparent sheet in the light beams, said computer system including a processing means for calculating and storing angular deviation values of the transparent sheet as a function of the signals and a processing means for calculating distortion values of the transparent sheet as a function of the angular deviation values; and output means for selectively displaying the angular deviation values and the distortion values of the transparent sheet.

2. The apparatus for evaluating optical quality defined in claim 1, wherein said computer system includes means for storing a range of acceptable distortion values for the transparent sheet, for comparing the calculated distortion values to the stored distortion values, and for characterizing the transparent sheet as defective when the calculated distortion values exceed the range of acceptable distortion values.

3. The apparatus for evaluating the optical quality defined in claim 1, wherein said positioning means includes a drive means for controlling the position of the transparent sheet and for passing the transparent sheet through the beams of light in a controlled manner to obtain a plurality of angular deviation values for the transparent sheet.

4. The apparatus for evaluating the optical quality defined in claim 1, wherein said computer system transmits the plurality of angular deviation values to said output means for displaying the angular deviation values.

5. The apparatus for evaluating optical quality defined in claim 1, wherein said positioning means includes a conveyor for engaging a portion of the transparent sheet, said conveyor means having a center aperture to facilitate passing of the light beams through the transparent sheet.

6. The apparatus for evaluating optical quality defined in claim 1, including a key board connected to said computer system for inputting data and instructions to said computer system.

7. The apparatus for evaluating optical quality defined in claim 1, wherein said output means includes a monitor for displaying angular deviation values, distortion values, and other information regarding the transparent sheet.

8. The apparatus for evaluating optical quality defined in claim 7, wherein said computer system calculates a plurality of angular deviation values and the monitor displays the plurality of angular deviation values.

9. The apparatus for evaluating optical quality defined in claim 8, wherein said computer system calculates a plurality of distortion values and the monitor displays the plurality of distortion values.

10. The apparatus for evaluating optical quality defined in claim 7, wherein the angular deviation values are displayed as a color-coded map of the transparent sheet.

11. The apparatus for evaluating the optical quality defined in claim 1, wherein said light sources are positioned in a linear arrangement with parallel light beams.

12. The apparatus for evaluating the optical quality defined in claim 11, wherein said positioning means is a conveyor and the linear arrangement of said light sources is transverse to a path of the conveyor.

13. The apparatus for evaluating the optical quality defined in claim 1, wherein said light sources are laser light sources with polarized light beams.

14. The apparatus for evaluating the optical quality defined in claim 1, wherein said light sources are collimated light sources.

15. The apparatus for evaluating the optical quality defined in claim 13, including beam expanders aligned with said laser light sources.

16. The apparatus for evaluating the optical quality defined in claim 1, wherein said photosensitive position detectors are four quadrant photo detectors.

17. The apparatus for evaluating the optical quality defined in claim 1, including an adjustable mounting mechanism for each lens such that each lens may be positioned at a distance from the photosensitive position detectors equal to its focal length.

18. The apparatus for evaluating the optical quality defined in claim 1, including a frame for mounting and positioning the plurality of light sources and the corresponding plurality of lenses and photosensitive position detectors on opposite sides of the transparent sheet transported on the positioning means such that the light beams pass through the transparent sheet at an angle.

19. The apparatus for evaluating the optical quality defined in claim 18, wherein said frame includes an adjustment means for varying the angle at which the beams of light pass through the transparent sheet by changing the position of said plurality of light sources and said corresponding plurality of lenses and photosensitive position detectors.

20. The apparatus for evaluating the optical quality defined in claim 18, wherein said frame includes a pair of side members and a pair of end members defining a generally rectangular aperture through which the transparent sheet is transported, said plurality of light sources mounted on one end member and said corresponding plurality of lenses and photosensitive position detectors mounted on the opposite end member and aligned with said light sources, and said side members rotatably mounted to a base such that the angle at which the beams of light pass through the transparent sheet may be changed by rotating the base.

21. The apparatus for evaluating the optical quality defined in claim 18, wherein said frame includes a motor and control system for selectively adjusting the angle at which the light passes trough the transparent sheet.

22. The apparatus for evaluating the optical quality defined in claim 1, wherein said computer system includes a filter to filter the signals from said detectors.

23. A method for inspecting transparent sheets for optical defects in a production process, said method comprising:

transporting transparent sheets between a plurality of parallel, spaced-apart light sources and a corresponding plurality of lenses with photosensitive position detectors positioned at a focal point of the lenses;

simultaneously directing beams of light from said light sources through the transparent sheets to the lenses and the photosensitive position detectors;

generating angular deviation signals as a function of the change in position of the light beams on the photosensitive position detectors;

transmitting angular deviations signals from the photosensitive position detectors to a computer system; and calculating an angular deviation value for one or more areas of the transparent sheets.

24. The method for inspecting a transparent sheet for optical defects defined in claim 23, including an additional step of calculating a plurality of distortion values for the transparent sheet as a function of the angular deviation values.

25. The method for inspecting a transparent sheet for optical defects defined in claim 24 including the additional step of displaying the angular deviation values or distortion values for the transparent sheet on a monitor.

26. The method for inspecting a transparent sheet for optical defects defined in claim 23, including an initial step of inputting a range of acceptable angular deviation values for the transparent sheet into the computer system, and including final steps of comparing the calculated angular deviation values to the range of acceptable angular deviation values, and characterizing the transparent sheet as defective when one or more calculated angular deviation values exceed the range of acceptable angular deviation values.

27. The method for inspecting a transparent sheet for optical defects defined in claim 24, including an initial step of inputting a range of acceptable distortion values for the transparent sheet into the computer system, and including final steps of comparing the calculated distortion values to the range of acceptable distortion values, and characterizing the transparent sheet as defective when one or more calculated distortion values exceed the range of acceptable distortion values.

28. The method for inspecting a transparent sheet for optical defects defined in claim 23, including the initial step of adjusting the position of the light sources, lenses and photosensitive position detectors such that the light beams are directed through the transparent sheet at a viewing angle of the transparent sheet.

29. Apparatus for evaluating the optical quality of a transparent sheet being transported in a production operation, said apparatus comprising:

positioning means for positioning and transporting a transparent sheet;

a plurality of light sources mounted on a frame adjacent said positioning means, said light sources arranged in spaced apart relationship for directing a plurality of generally parallel light beams toward the transparent sheet;

a corresponding plurality of lenses mounted on the frame for focusing the light beams, said plurality of lenses mounted opposite the transparent sheet from said plurality of light sources;

a corresponding plurality of photosensitive position detectors positioned at a focal point of said plurality of lenses and aligned with said plurality of light sources for detecting the light beams and for generating signals indicative of the position of the light beams;

a computer system in electrical communication with said plurality of photosensitive position detectors for processing the signals received from said photosensitive position detectors as said positioning means transports the transparent sheet through the light beams, said computer system including a processing means for calculating angular deviation values of the transparent sheet as a function of the signals; and output means for selectively displaying the angular deviation values of the transparent sheet.

30. The apparatus for evaluating the optical quality defined in claim 29, including a processing means having a differentiation circuit for calculating distortion values as a function of the rate of change of the signals.

* * * * *